US009155924B1

(12) United States Patent
Grove et al.

(10) Patent No.: US 9,155,924 B1
(45) Date of Patent: Oct. 13, 2015

(54) MODULAR CHEMICAL/BIOLOGICAL HEADGEAR SYSTEM

(75) Inventors: Corey M. Grove, Red Lion, PA (US); Stephen E. Chase, Jarrettsville, MO (US); Daniel J. Barker, Fawn Grove, PA (US)

(73) Assignee: The United States of America as Represented by the Secretary of the Army, Washington, DC (US)

( * ) Notice: Subject to any disclaimer, the term of this patent is extended or adjusted under 35 U.S.C. 154(b) by 2004 days.

(21) Appl. No.: 11/672,570

(22) Filed: Feb. 8, 2007

(51) Int. Cl.
| | |
|---|---|
| *A62B 18/04* | (2006.01) |
| *A62B 18/02* | (2006.01) |
| *A62B 18/08* | (2006.01) |
| *A61M 16/06* | (2006.01) |
| *A62B 7/10* | (2006.01) |
| *A62B 23/02* | (2006.01) |
| *A42B 3/28* | (2006.01) |

(52) U.S. Cl.
CPC ............... *A62B 18/04* (2013.01); *A42B 3/288* (2013.01); *A61M 16/0627* (2014.02); *A62B 7/10* (2013.01); *A62B 18/02* (2013.01); *A62B 18/08* (2013.01); *A62B 23/02* (2013.01); *A42B 3/28* (2013.01)

(58) Field of Classification Search
CPC .............. A62B 7/00; A62B 7/10; A62B 9/00; A62B 17/00; A62B 17/04; A62B 18/00; A62B 18/02; A62B 18/025; A62B 18/04; A62B 18/045; A62B 18/08; A62B 18/082; A62B 18/084; A62B 18/006; A62B 23/02; A62B 17/006; A62B 17/008; A42B 3/28; A42B 3/288; A42B 3/08; A42B 3/003; A61M 16/0683; A61M 16/06; A61M 16/0627

USPC ............ 128/201.24, 201.22, 201.23, 201.25, 128/201.29, 206.12, 206.16, 206.17; 2/6.1, 2/6.2, 6.6, 6.7, 410, 422–425
See application file for complete search history.

(56) References Cited

U.S. PATENT DOCUMENTS

| | | | | |
|---|---|---|---|---|
| 3,822,698 | A * | 7/1974 | Guy ......................... | 128/201.25 |
| 5,054,480 | A * | 10/1991 | Bare et al. ................ | 128/201.25 |
| 5,283,914 | A * | 2/1994 | James ....................... | 2/424 |
| 5,711,033 | A * | 1/1998 | Green et al. ............... | 2/171.3 |
| 6,176,239 | B1 * | 1/2001 | Grove et al. ............. | 128/206.24 |
| 6,401,259 | B1 * | 6/2002 | Epperson et al. ............ | 2/410 |
| 6,513,168 | B2 * | 2/2003 | Paris et al. ................. | 2/171.3 |
| 6,763,835 | B1 * | 7/2004 | Grove et al. ............... | 128/857 |
| 6,766,537 | B1 * | 7/2004 | Maki et al. ................. | 2/171.3 |
| 6,810,532 | B2 * | 11/2004 | Wang Lee .................. | 2/171.3 |
| 6,826,783 | B1 * | 12/2004 | Grove et al. ............... | 2/424 |
| 6,990,691 | B2 * | 1/2006 | Klotz et al. ................ | 2/171.3 |
| 7,028,688 | B1 * | 4/2006 | Grove et al. ............. | 128/201.25 |
| 7,051,732 | B2 * | 5/2006 | Uusitalo et al. ........... | 128/201.25 |
| 2007/0000031 | A1 * | 1/2007 | Makris et al. ............... | 2/411 |
| 2007/0289592 | A1 * | 12/2007 | Sutton et al. .............. | 128/201.24 |
| 2008/0276933 | A1 * | 11/2008 | Dampney et al. .......... | 128/201.25 |

\* cited by examiner

Primary Examiner — Justine Yu
Assistant Examiner — Colin W Stuart
(74) Attorney, Agent, or Firm — Ulysses John Biffoni

(57) ABSTRACT

A modular chemical/biological headgear system includes a helmet liner of a resilient shock absorbing material that conforms generally to the shape of a wearer's head, provides a cavity for removable installation of one or more modular filters in the back, and a duct to convey filtered air from the one or more modular filters to a face mask. The helmet liner may be equipped and configured with a variety of interchangeable modular components including hardened outer shells, communications modules, enhanced chemical biological filters, and the like, to meet a wide variety of operational needs.

15 Claims, 6 Drawing Sheets

MODULAR CHEMICAL/BIOLOGICAL HEADGEAR SYSTEM

GOVERNMENT INTEREST

The invention described herein may be manufactured, licensed, and used by or for the U.S. Government.

TECHNICAL FIELD

The present invention relates in general to helmets and other headgear that integrate air-purifying filters and masks and in particular to a modular helmet liner system that integrates air-purifying alters and a face mask, as well as other components in or together with a helmet liner.

BACKGROUND

Historically, air-purifying respirator masks such as those intended for protection against chemical and biological agents were not specifically designed for use in combination with helmets, headsets, and other head mounted gear. Increasingly, however, military, homeland security, and civilian law enforcement personnel are required to wear chemical/biological air purifying filtration apparatus along with helmets, headsets, face shields and other head mounted gear. The lack of integration between traditional respirator masks and other head mounted equipment has caused discomfort, difficulty in fitting and obtaining a proper air seal, premature fatigue and diminished capabilities for wearers, especially after extended periods of use. The addition of night vision goggles, communications gear, and Other head mounted apparatus further exacerbates the problem.

Various efforts have been directed to integrating air-purifying filtration apparatus with head mounted gear. One example is found in U.S. Pat. No. 6,826,783 issued on Dec. 7, 2004 to Grove, et al., a co-applicant herein ("'783 patent"), and is incorporated by reference in its entirety. The '783 patent discloses a chemical/biological protection helmet, especially suited to use by aircraft personnel, that incorporates a self-contained air-purifying filter system to provide protection against a range of chemical and biological agents. The air-purifying filter in the '783 patent is attached to the helmet behind the wearer's head. Ducting within the helmet connects the rear mounted filter to the front to provide filtered air to the user. Placement of the filter behind the head advantageously positions the center-of-gravity of the helmet system closer to a point lying over the shoulders of the wearer. This results in improved stability and comfort and removes the filter from the wearer's field of view for better visibility. While the '781 patent provides significant improvements over the prior art, further improvements are needed, particularly in the areas of operational flexibility and modularity. For example, components of the '783 patent's chemical/biological protection helmet are not configured to be interchangeably incorporated into different chemical/biological personal protection systems. In addition, reconfiguration of system component parts to meet different operational needs is limited. Embodiments according to the present invention are designed to address at least the foregoing needs.

SUMMARY

In general, in one aspect, an embodiment of a modular chemical/biological headgear system according to the present invention includes a helmet liner of a resilient shock absorbing material that conforms generally to the shape of a wearer's head and that provides a cavity for removable installation of one or more modular filters in the back, and a duct to convey filtered air from the one or more modular filters to a face mask wherein the helmet liner may be equipped and configured with a variety of interchangeable modular components to meet a variety of operational needs. Optional modular component may include a hardened outer shell, a communications module, an enhanced chemical biological filter, and the like.

DETAILED DESCRIPTION

In the following detailed description, reference is made to the accompanying drawings. The drawings are a part of this disclosure and illustrate specific embodiments in which the invention, as claimed, may be practiced. The invention, however, may be embodied in many different forms and should not be construed as limited to the embodiments set forth; rather, these embodiments are provided so that this disclosure will be thorough and complete, and will fully convey the scope of the invention to those skilled in the art. As will be appreciated by those of skill in the art, the present invention may be embodied in methods, systems and devices. Wherever possible, the same reference numbers will be used throughout the drawings to refer to the same or like parts. The term "helmet liner" as used herein refers generally to any energy absorbing head covering component whether or not it is intended to be worn together with an outer shell or helmet. In some embodiments according to the present invention, a system may be equipped with a removable outer shell that may be attached over the helmet liner for added head protection. In other embodiments, the system may not be equipped with a removable outer shell.

Embodiments according to the present invention are expected to significantly expand the utility of personal chemical-biological air-purifying respiratory filter systems by incorporating modular components. The term "modular" as used herein indicates they are constructed according to standardized dimensions and interfaces.

The term "modular" as used herein refers to substantially standardized dimensions and interfaces to facilitate assembly, reconfiguration and replacement of components and to provide interchangeability of components among different systems. Systems according to the present invention generally include modular components that may be assembled, configured and/or reconfigured into systems tailored to meet different operational needs. For example, modular components may be selected for a particular headgear system based on the need to provide a higher level CB protection or to provide protection against certain types of CB contaminants. Other modular components may be selected for a headgear system based on the need for greater head protection, improved thermal insulation or cooling, camouflage, more advanced communications, or other capabilities. The use of modular components may also simplify design and development of new components by virtue of their standardized dimensions and interfaces.

Figure 1:
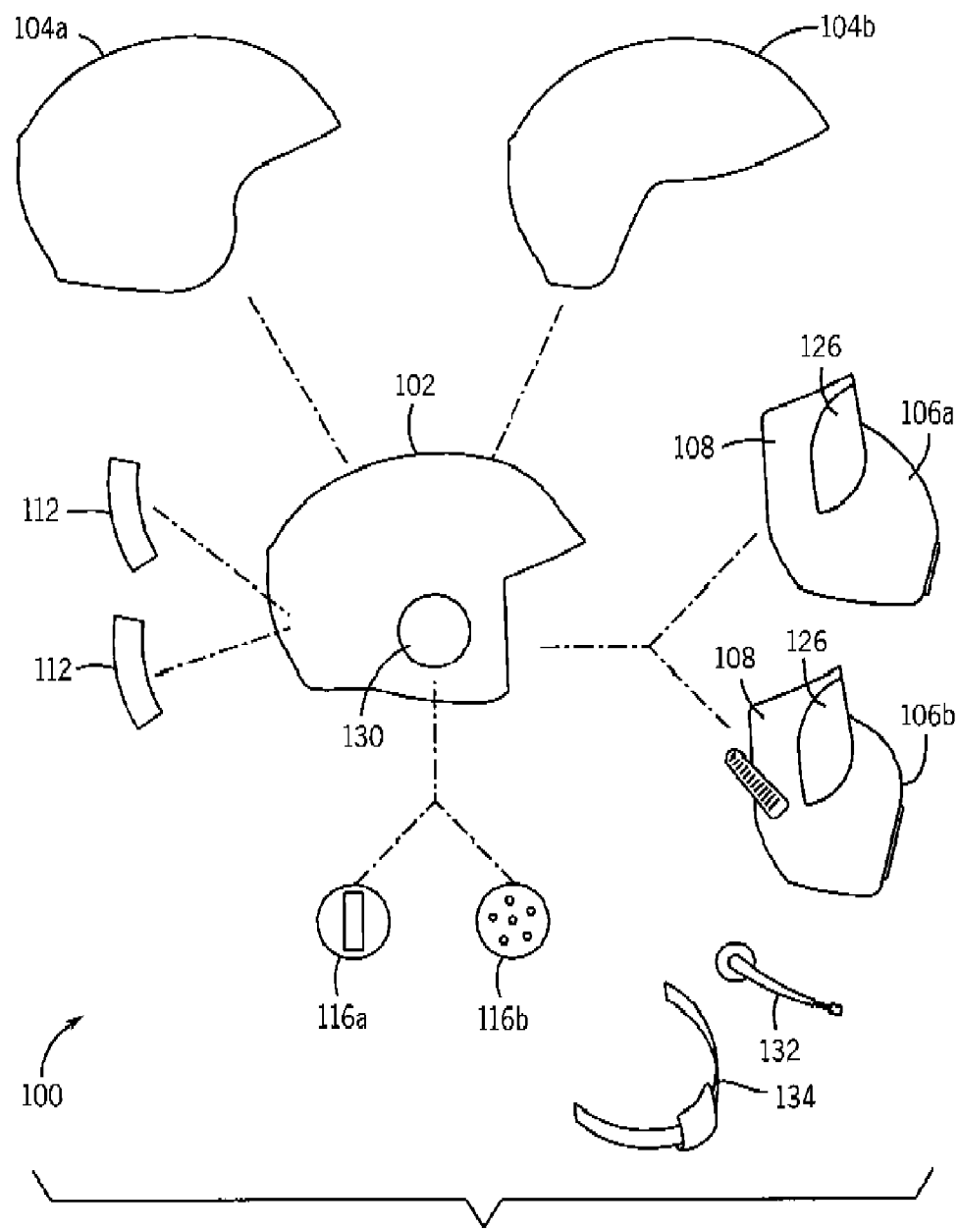
FIG. 1 shows a schematic representation of a modular chemical/biological headgear system according to the present invention.
Figure 2:
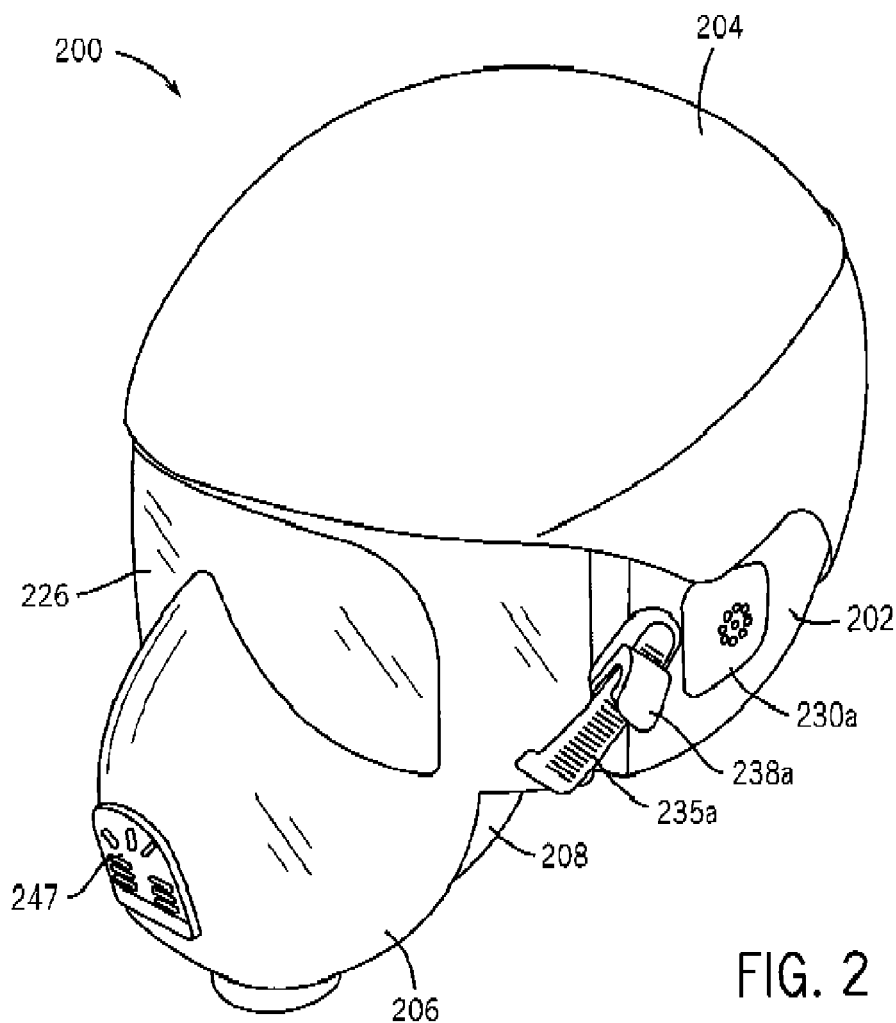
FIG. 2 shows a perspective view of a preferred embodiment of a modular chemical/biological headgear system according to the present invention.

FIG. 1 shows a schematic representation of a modular chemical/biological headgear system 100 according to the present invention. At the center of modular chemical/biological headgear system 100 is a universal helmet liner 102. Liner 102 is a dome-shaped head covering of a resilient shock absorbing material that conforms generally in shape and size to a wearer's head. Liner 102 extends to the middle of the forehead in front, over the ears on the sides, and just above the nape of the neck in the back. The material selected for liner 102 should be lightweight, possess good dimensional stability and have excellent energy absorbing properties. In the preferred embodiment, a semi-rigid polyurethane plastic energy absorbing foam has been used to construct liner 102. Other low density rigid or semi-rigid plastic foams such as expanded polypropylene (EPP), expanded polystyrene (EPS), expanded polyphenylene oxide/polystyrene (EPPE/PS) or similar may be selected. Liner 102 provides a frame to which auxiliary and/or alternative system components may be attached internally and/or externally. Foam suspension pads of different thicknesses may be attached to the inside of liner 102 via hook and loop fasteners, or similar, to provide a range of sizing alternatives and maintain the headgear system 100 in proper position. Liner 102 provides one or more cavities for installation of internal or external modular components. The liner also includes points of attachment with standardized dimensions and fasteners for installation of external or internal modular components.

In applications where additional head protection is needed, a hardened outer shell 104 may be added over liner 102. Two versions are shown in FIG. 1. Shell 104a includes additional protection on the side of the head and fully covers the wearer's ears while shell 104b is an open ear version. Shell 104 is preferably made from a rigid, light weight impact resistant material that has good resistance to projectile penetration, such as fiberglass, ABS, a polycarbonate, a composite material, or an aramid fiber ballistic shell material (e.g., Kevlar®) or combinations thereof. Shell 104 can be attached to liner 102 with hook and loop (Velcro) strips, adhesive strips, clips, buckles, snaps, or other similar small fasteners. Shell 104 may be composed of a single layer or may include multiple layers. Depending on operational needs, other materials may be selected for use in shell 104 to provide properties such as heat shielding, inflammability, electromagnetic shielding, and chemical resistance.

A facemask module 106 that covers and protects the nose and mouth and eyes may also be attached to liner 102. Facemask 106 is made, in part, from a material that is flexible and resilient and that provides a good air seal around the nose and mouth, and typically, the entire face, such as a natural or synthetic rubber. As shown in FIG. 1, a visor 126 is integrated with facemask module 106, extending upwardly to cover the area of the wearer's eyes and forehead. Visor 126 is made from an optically transparent impact resistant material such as polyurethane or polycarbonate. In alternative embodiments, visor 126 may be provided as a separate, removable component. Shown in FIG. 1 are two representative and alternative facemask modules 106. Facemask module 106a includes secondary filtration capability for enhanced or extended duration chemical biological protection, whereas facemask module 106b does hot include a secondary filtration capability. A face seal 108 of a synthetic or organic rubber material is provided around the edge of facemask modules 106a and 106b. Face seal 108 forms a flexible and substantially airtight seal between the face of the user and facemask module 106 to prevent contaminated air from breaching the system. Face seal 108 may be bonded, clamped, or molded to facemask module 106.

One or more filter modules 112 for filtering chemical and biological contaminants are incorporated into modular chemical/biological headgear system 100. As shown in FIG. 1, two filter modules 112 may be disposed in one or more cavities located in the rear of helmet liner 102. Various alternate filter modules 112 may be employed depending on the chemical and biological protection requirements of a particular application. Interfaces for external filtering and air supply equipment may also be attached or substituted for filter modules 112. Such interfaces may provide ports for attachment to powered air purification or self-contained breathing apparatus (SCBA) systems including connections to portable air purification/air supply units or connections to multi-user air purification/air supply systems such as may be provided in a vehicle.

Communications modules 116 may be included in embodiments of chemical biological headgear system 100. Communications modules 116 include non-electronic communications modules 116a, i.e., units to provide ear protection and to improve audibility during mask deployment; as well as electronic communications modules 116b which may provide additional capabilities. Communication modules 116 are preferably sealed to protect the wearer from contamination. Non-electronic communications modules 116a may be inserted into ear module openings 130 on either side of the helmet liner 102 to provide cushioning and added protection from lateral blows. Such non-electronic communication modules may also be configured to include passive noise reduction and filtering to protect the wearer against high decibel sounds from gun fire and explosions while providing a pass band at lower decibels to enable good transmission of voice communication. Electronic modules 116b may be inserted into ear openings 130. Electronic modules 116b may be wired or wireless and may include headset receivers (ear phones), sound absorbing cushioning ear cups and the like. One or more microphones for voice communication, noise canceling and the like may be provided inside and/or outside of mask module 106. A boom microphone 132 for attachment to helmet liner 102 is shown in FIG. 1. Active noise reduction/canceling or noise filtering systems may also be incorporated in helmet liner systems according to the present invention. Ear phones and microphones are preferably adjustable to enable the wearer to place them in proper position and in comfortable relationship with the user's ears and mouth, respectively.

Headgear system 100 may also include one or more head retainer straps such as a chin strap 134 to firmly secure the headgear to the wearer's head. Chin strap 134 extends under the chin of the wearer and adjustably connects to retainers secured to helmet liner 102 on opposite sides of the wearer's head. Releasable fasteners (not shown) on either side of the helmet liner 102, preferably including quick release and ratcheting adjustability, are preferably provided to enable rapid release, installation and adjustment of chin strap 134 and rapid removal of helmet/helmet liner systems according to the present invention. In alternative embodiments, a rear strap may also be provided behind the wearer's neck to ensure the helmet is secured to the head from the back as well as the front.

FIGS. 2-7 show an embodiment of a modular chemical-biological helmet liner system 200 according to the present invention that includes a hard-shell helmet. Helmet liner system 200 is especially suited to use by ground personnel who require chemical and biological breathing apparatus, substantial head armor and full visor protection. Helmet liner system 200 includes a universal liner 202, a hard-shell helmet 204 that is releasably attached to the outside of liner 202, a facemask module 206 that integrates a visor 226, a face seal 208 that provides a substantially airtight seal between facemask module 206 and the wearer's face and a pair of identical filter modules 212a and 212b. Facemask module 206 is secured to liner 202 by left and right facemask straps 235a and 235b positioned on either side of the mask. Facemask straps 235a and 235b are received by corresponding strap fasteners 238a and 238b on either side of liner 202. As the facemask straps 235 are tightened, face seal 208 is pressed against the wearer's face to form a substantially airtight seal therewith. A top edge 207 and side edges 209 around facemask module 206 and visor 226 are also engaged by an edge seal 203 of an elastic material formed around the forward edge of helmet liner 202. In alternative embodiments, a single facemask strap may be employed on one side only, with a hinge, hook and eye, or similar fastener, positioned on the opposite side.

A nose cup assembly 210, shaped generally to cover the nose and mouth of the wearer and made from a pliable, resilient material such as natural or synthetic rubber so as to seal comfortably against the wearer's face, is provided inside facemask module 206. Nose cup assembly 210 serves to minimize fogging and reduce CO2 build-up within facemask module 206. Nose cup assembly 210 may be integrated with facemask module 206 in this embodiment, or may be a separable and removable component.

Figure 7:
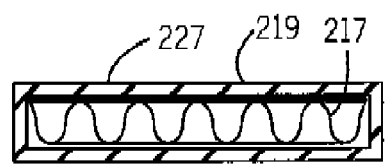
FIG. 7 shows a side sectional view of the duct shown in FIG. 6.
Figure 3:
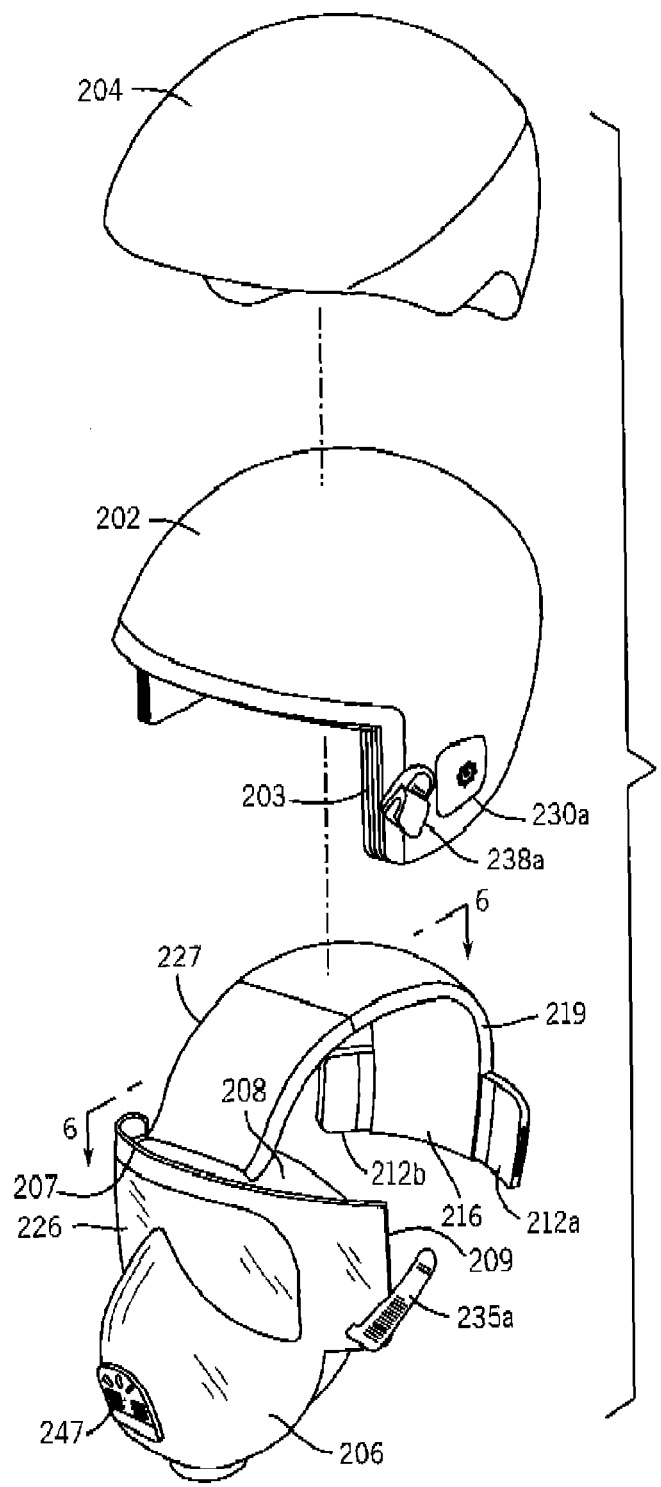
FIG. 3 shows an exploded view of the modular chemical/biological headgear system shown in FIG. 2.
Figure 4:
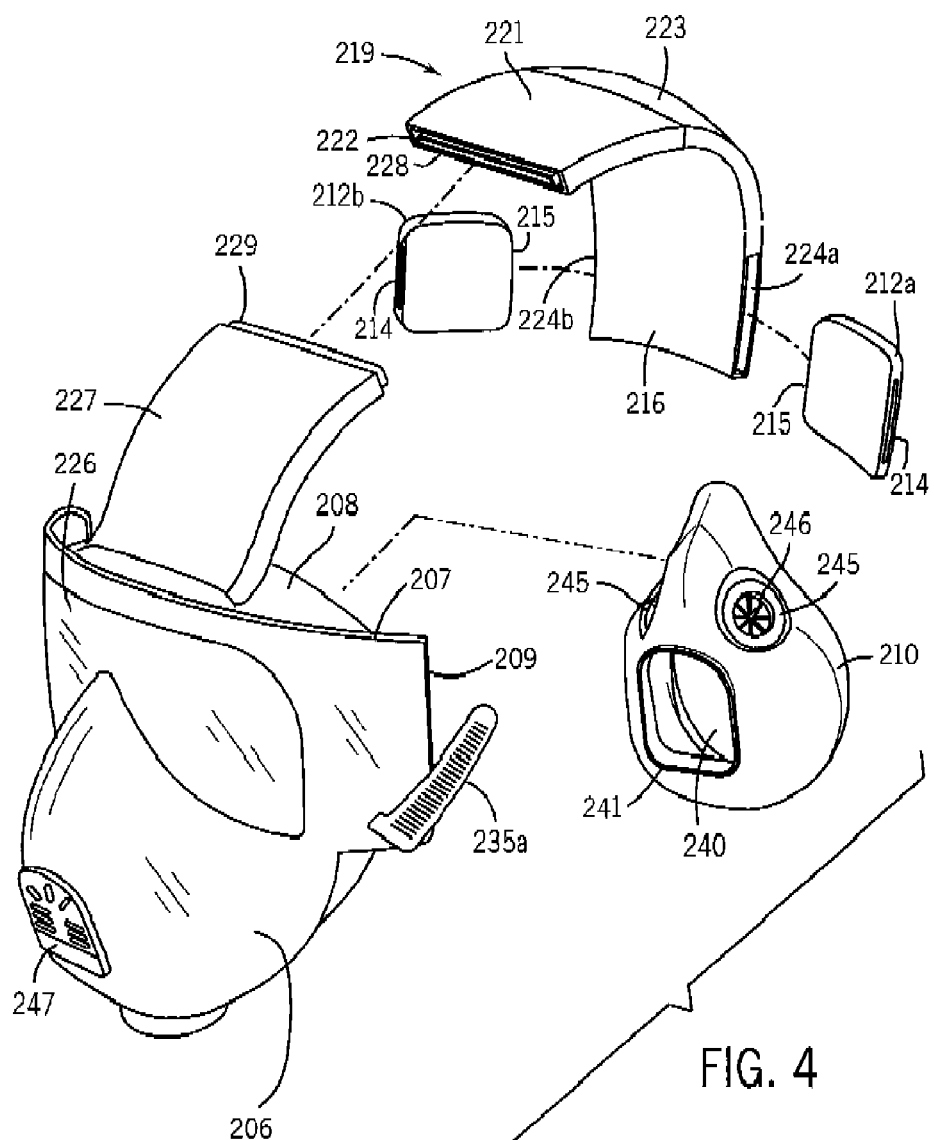
FIG. 4 shows an exploded view of internal components of the modular chemical/biological headgear system shown in FIG. 2 including a mask module, nose cup, ducts and filter modules.
Figure 5:
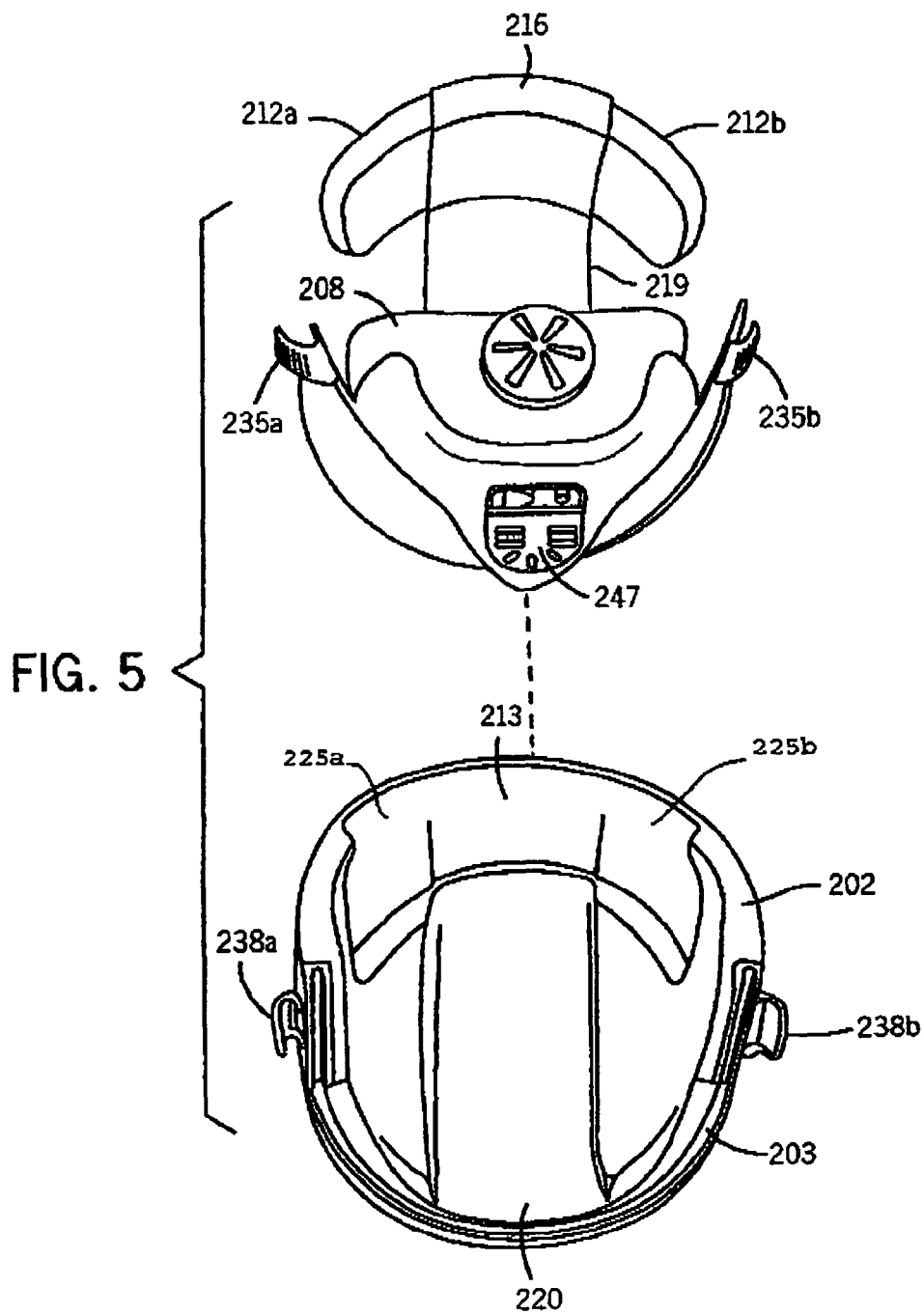
FIG. 5 shows a perspective view from the bottom of the inside of the helmet liner of FIG. 2 separated from the mask module, ducts and filter modules.
Figure 6:
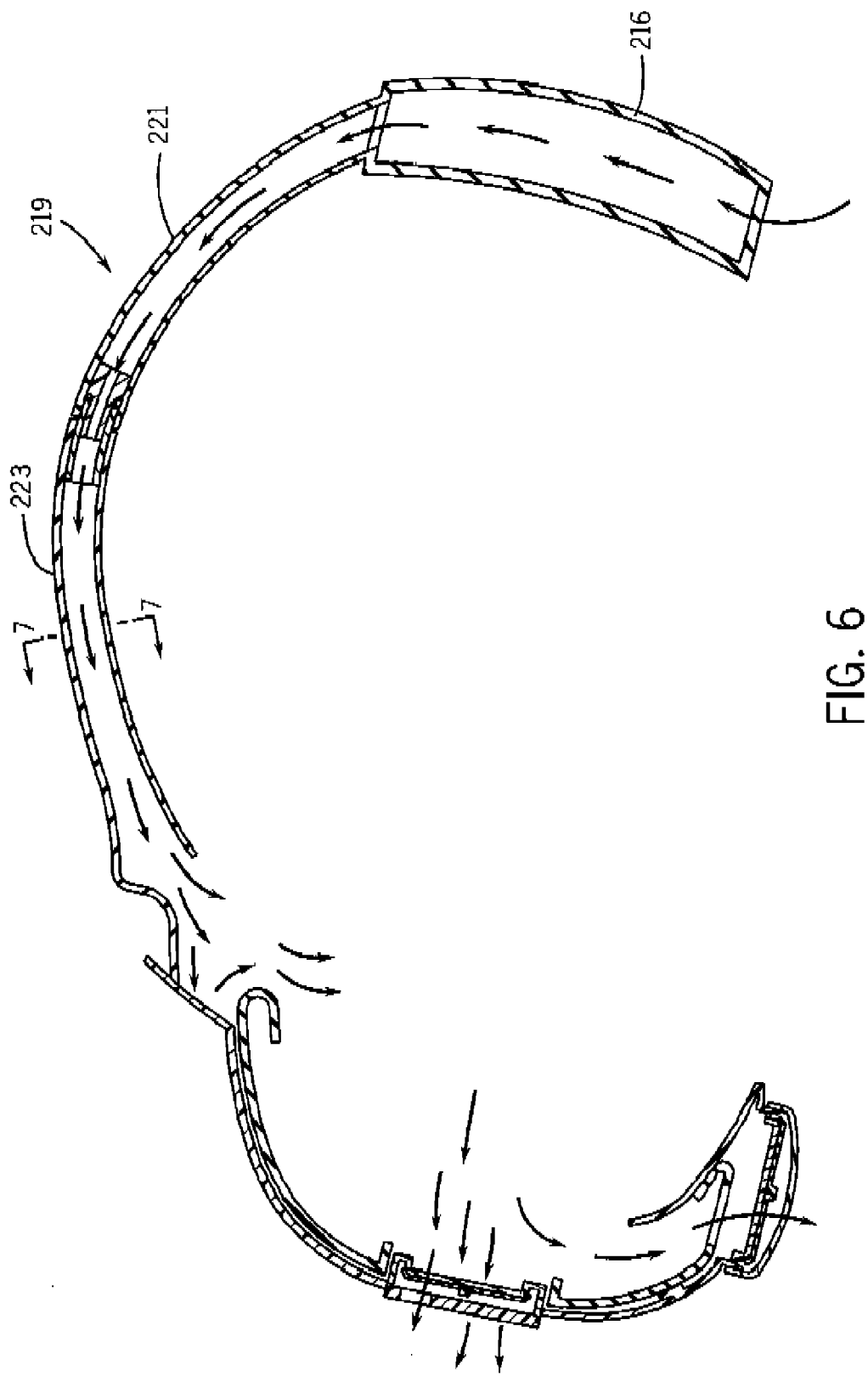
FIG. 6 shows a side sectional view of the mask module of FIG. 2 attached to ducts and filter modules.

Filter modules 212a and 212b are installed in a rear lateral cavity 213 located inside helmet liner 202. Lateral cavity 213 extends substantially across the back of helmet liner 202 at the bottom and includes left and right filter receiving spaces 225a and 225b. Filter modules 212a and 212b are described in more particularity in application Ser. No. 11/533,060, filed on behalf of Corey Grove, et al., on Sep. 19, 2006, entitled "High Surface Area Chemical/Biological Filter," and incorporated herein by reference as if fully set forth. Each filter module 212a/212b includes an air inlet 214 and an air outlet 215. Filter modules 212a and 212b are positioned such that air inlets 214 are exposed to the outside air behind the wearer's head. A lateral duct 216 is positioned between filter modules 212a and 212b and provides left and right filter ports 224a and 224b. Ports 224a and 224b receive filter modules 212a and 212b and provide a substantially airtight coupling of air outlets 215 to lateral duct 216. Lateral duct 216 is pneumatically coupled to a longitudinal head duct 219. Longitudinal head duct 219 is disposed in a longitudinal cavity 220 that runs from lateral cavity 213 to the front of helmet liner 202 and extends forward over the head of the wearer to convey air from filter modules 212a and 212b to facemask module 206. Longitudinal duct 219 preferably separates into two duct sections 221 and 223 to facilitate cleaning and filter replacement. Duct sections 221 and 223 are joined at an air tight seal using a low profile clamping mechanism. Head duct 219 has an outlet port 222 at the front that pneumatically and removably couples to an air inlet port 229 of a forward duct 227. The back end of forward duct 227 extends up from the top of facemask module 206, conforming in shape to longitudinal cavity 220, and curves rearward to meet outlet port 222. The forward end of forward duct 227 terminates at an outlet port 228 inside of facemask module 206 at the top. Fresh air drawn into the mask module 206 through outlet port 228 passes over the inside of visor 226 and thus helps to reduce fogging. Outlet port 228 is preferably covered with a mesh/spacer to prevent dust and debris from entering the passage and prevent the duct from collapsing. As shown in FIG. 7, longitudinal duct 219 includes a spacer medium 217 on the inside of a resilient flexible rubber or plastic material to prevent the duct from collapsing or the airflow from becoming restricted while at the same time enabling the duct to be flexible and shock absorbing. Spacer medium 217 is preferably corrugated or fluted to form a number of parallel channels running the length of the duct to avoid restricting airflow.

A nose cup assembly 210, made of a flexible, resilient material such as natural or synthetic rubber, is provided inside facemask 206, Nose cup 2W may be integrated with facemask 206 or may be provided as a separate, removable component. Nose cup 210 includes a forward opening 240 that is coupled to an exhaust port 247 provided in facemask module 206 in front of the wearer's mouth. Exhaust port 247 allows exhaled air to be exhausted and is equipped with a conventional one way exhalation valve (not shown) to prevent the inhalation of contaminated air. Forward opening 240 provides a soft grommet-like edge that engages a corresponding hard plastic ridge provided around the inside opening of exhaust port 247 to secure nose cup 210 in position and ensure that a good air seal is provided. Exhaled air is thus channeled and exhausted directly from nose cup 210 and is not allowed to circulate inside facemask module 206 in order to minimize fogging and reduce $CO_2$ build-up. Inhalation ports 245 are provided in nose cup 210 to enable fresh air to be drawn in through facemask module. Inhalation ports 245 are equipped with conventional inhalation valves 246 to prevent back flow of exhaled air into facemask module 206.

While ducts 216 and 219 are shown as separable in this embodiment, and duct 219 is divided into duct sections 221 and 223, in alternative embodiments, ducts 216 and 219 and duct sections 221 and 223 may be integrated. Likewise, in some alternative embodiments of helmet liner systems according to the present invention, ducts may be formed integrally with the helmet liner.

CONCLUSION

As has been shown, embodiments according to the present invention provide a modular chemical-biological helmet liner system that includes modular components. The modular components have substantially standardized dimensions and interfaces to facilitate interchangeability, rapid assembly and incorporation in a variety of personal respiratory protection systems. The modular components may be reconfigured to meet a variety of operational needs. A number of embodiments of the invention defined by the following claims have been described. Nevertheless, it will be understood that various modifications to the described embodiments may be made without departing from the spirit and scope of the claimed invention. Accordingly, other embodiments axe within the scope of the invention, which is limited only by the following claims.

What is claimed is:

1. A modular chemical-biological headgear system, comprising:
   a helmet liner that is adapted to conform generally to the shape of a wearer's head and which includes a longitudinal cavity adapted for removable installation of a longitudinal duct, and a rear lateral cavity adapted for removable installation of a lateral duct and a modular filter;

a facemask module that is releasably attachable to the helmet liner and is adapted to be sealable to the face of the wearer;

an exhaust port to enable exhausted air to be vented from the facemask module;

a nose cup assembly that is adapted to form a seal over the wearer's nose and mouth and is pneumatically coupled to the exhaust port to prevent exhausted air from circulating inside the facemask module; and wherein when installed said longitudinal duct is disposed in said longitudinal cavity and couples to the lateral duct and facemask module to convey filtered air from the modular filter to the facemask module, and wherein the longitudinal duct and modular filter are removable from the helmet liner.

2. The modular chemical-biological headgear system of claim 1, wherein the helmet liner comprises an energy absorbing material.

3. The modular chemical-biological headgear system of claim 1, wherein the helmet liner is comprised of a semi-rigid energy absorbing foam.

4. The modular chemical-biological headgear system of claim 1, wherein the helmet liner is adapted to extend over the ears of the wearer.

5. The modular chemical-biological headgear system of claim 1, holier comprising an outer shell or helmet composed of a rigid, light-weight, impact resistant material adapted to be installed over the helmet liner.

6. The modular chemical-biological headgear system of claim 1, wherein the facemask module includes a visor.

7. The modular chemical-biological headgear system of claim 6, wherein the longitudinal duct to convey filtered air from the modular filter to the facemask module includes an outlet port that is positioned above the visor to cause fresh air to pass over an inside surface of the visor and reduce fogging.

8. The modular chemical-biological headgear system of claim 1, wherein the facemask module includes a face seal that is adapted to form a flexible and substantially airtight seal between the face of the wearer and the facemask module.

9. The modular chemical-biological headgear system of claim 1, wherein the longitudinal duct to convey filtered air from the modular filter to the facemask module is adapted to run substantially over the top of the wearer's head.

10. The modular chemical-biological headgear system of claim 1, wherein the center-of-gravity of the system is adapted to be located substantially over the shoulders of the wearer.

11. The modular chemical-biological headgear system of claim 1, wherein the helmet liner is adapted to extend substantially to mid-forehead of the wearer in front and substantially to the nape of the neck in back.

12. The modular chemical-biological headgear system of claim 1, wherein the longitudinal duct is comprised of pneumatically coupled sections.

13. The modular chemical-biological headgear system of claim 1, wherein the longitudinal duct is comprised of a resilient shock absorbing material.

14. The modular chemical-biological headgear system of claim 1, wherein the longitudinal duct includes a spacer medium to prevent collapse and restriction of airflow.

15. The modular chemical-biological headgear system of claim 1, wherein the nose cup assembly is removable from the facemask module.

\* \* \* \* \*